US006799571B1

(12) United States Patent
Hughes et al.

(10) Patent No.: US 6,799,571 B1
(45) Date of Patent: Oct. 5, 2004

(54) MEDICINAL POWDER DELIVERY SYSTEM

(75) Inventors: Nathaniel Hughes, Palm Springs, CA (US); Leon Shaw, Santa Monica, CA (US)

(73) Assignee: Molecular Rotation, LLC, Concord, CA (US)

( * ) Notice: Subject to any disclaimer, the term of this patent is extended or adjusted under 35 U.S.C. 154(b) by 0 days.

(21) Appl. No.: 10/401,848

(22) Filed: Mar. 31, 2003

Related U.S. Application Data

(60) Provisional application No. 60/389,787, filed on Jun. 19, 2002.

(51) Int. Cl.[7] ................................................ A61M 15/00

(52) U.S. Cl. .............................. 128/203.12; 128/203.15

(58) Field of Search ....................... 128/200.14, 200.18, 128/200.21, 200.22, 200.24, 203.12, 203.14, 203.15, 203.18, 203.19, 203.21, 203.22, 203.23, 204.14; 239/290, 302, 310, 311, 312, 368–370, 461, 463, 466, 472, 474, 477; 604/58

(56) References Cited

U.S. PATENT DOCUMENTS

| | | | | | |
|---|---|---|---|---|---|
| 5,740,794 | A | * | 4/1998 | Smith et al. | 128/203.15 |
| 6,089,228 | A | * | 7/2000 | Smith et al. | 128/203.15 |
| 6,158,676 | A | * | 12/2000 | Hughes | 239/405 |
| 6,257,233 | B1 | * | 7/2001 | Burr et al. | 128/203.15 |
| 2001/0029948 | A1 | * | 10/2001 | Ingle et al. | 128/203.15 |

* cited by examiner

*Primary Examiner*—Teena Mitchell
(74) *Attorney, Agent, or Firm*—Theodore J. Bielen, Jr.

(57) ABSTRACT

A medicinal delivery system utilizing a gaseous propellant source. The system includes a nozzle having an entrance and exit for passing medicinal powder material threrethrough. A conduit is also utilized to direct gaseous propellant to a place adjacent the nozzle exit. A flow shaper produces a vortex stream of the gaseous propellant which mixes with the medicinal powder material exiting the nozzle. The medicinal powder, gaseous propellant, and air are mixed in a vessel chamber and forced from the vessel chamber through an exit for use as a homogeneous aerosol.

12 Claims, 4 Drawing Sheets

MEDICINAL POWDER DELIVERY SYSTEM

The present application claims the benefit of Provisional Application Serial No. 60/389,787, filed Jun. 19, 2002.

BACKGROUND OF THE INVENTION

The present invention relates to a novel and useful medicinal powder delivery system.

Drugs are often delivered in powder form to the lungs of patients, such as asthmatics, and powder medicaments offer several advantages over liquid drugs suspended in propellants in that powder medicaments are premixed and dosages of the same may be more accurately controlled. Also, powder medicaments are easier to manufacture and distribute since refrigeration is not often required.

Several problems arise with the use of powder medicaments. For example, it is essential that powders do not re-agglomerate before or at the time of delivery. Ideally, the delivery of powder medicaments should be in a "soft cloud" or homogeneous aerosol in which the particles constituting the powder remain separated, reagglomeration of particles into larger entities renders the powder as an incompatible entity to the alveolar tissue in the lungs. In other words, agglomerated powder medicaments act as irritants to the respiratory system. Typically, prior systems have mixed propellants with powder medicaments prior to delivery of the drug resulting in reagglomeration during storage or delivery of the mixture.

Also, it is important that powder medicaments not be contaminated before application to the lungs of a patient. Prior art systems employing fans and the like expose powder medicaments to potential contaminants during the delivery and storage process.

In addition, it is imperative that a constant and total dose of powder medicament be delivered to a patient in order to achieve a high percentage of absorption of the powder medicament by the alveolar tissue of the lungs. Again, the prior systems have not accomplished this result since dosage depends on various factors such as propellant pressure, timing, and velocity of propellant/powder streams, the ease of use, patient inhalation ability and the like. Also, many prior art powder drug delivery systems use gun-like mechanisms which create a high degree of stress on a patient, making them unsuitable in many cases.

A medicinal powder delivery system which is effective in safely and conveniently delivering drugs would constitute a remarkable advance in the medical field.

BRIEF SUMMARY OF THE INVENTION

In accordance with the present invention a novel and useful medicinal powder delivery system is herein provided.

The system of the present invention is used in conjunction with minimal quantities of a gaseous propellant of known characteristics. The system includes a nozzle having an entrance and exit for passing medicinal powder material through the same. The nozzle may be mounted or supported in a housing in a compact manner.

A conduit is also employed in the present invention and includes an entrance and exit for passage of a conventional gaseous propellant. The exit of the conduit lies adjacent the nozzle exit within the housing. In addition, the propellant is directed through means for shaping the flow of the characteristics of the gaseous propellant emanating from the gaseous propellant source and exiting the conduit. In this regard a stable vortex field is produced which creates a relatively high vacuum. Such means may take the form of a tube which includes an inner bore and an outer surface. The outer surface of the tube communicates with the conduit and may be formed with a plurality of recesses which interact with the propellant emanating from the gaseous propellant source and traveling through the gaseous propellant conduit. Each recess may be formed into one having a triangular cross-sectional configuration. The bore of the tube may further possess a first portion communicating with the nozzle exit and a second portion serving as an outflow for the powder medicament. In other words, the tube bore permits passage of the medicinal powder from the nozzle exit and outwardly from the tube bore. Most importantly, the outer surface of the tube possessing such means for shaping the flow characteristics of the propellant lies immediately adjacent the outflow of the tube.

A vessel having a chamber receives the outflow of powder medicament from the tube bore and the propellant flowing from the means for shaping the flow characteristics of the same. The gaseous propellant and the powder medicament are mixed in the chamber and expanded in the vessel. In this regard, the vessel may include an adjacent larger chamber having one or more vent openings to further mix the powder medicament and the gaseous propellant with air in the form of a homogeneous aerosol. The vessel includes an exit permitting egress of the medicinal powder, air, and relatively small amounts of propellant for delivery to a patient. The exit may include a plastic or elastomeric member having an opening of oval cross-sectional configuration to further control the movement of the aerosol.

Another aspect of the present invention concerns the storage and metering of the medicinal powder. In this regard, a support having a channel and an aperture may be formed on the housing to allow the aperture of the support to communicate with the entrance to the nozzle. The channel is intended to slidable engage items motivated therethrough.

A cartridge is also employed in the present invention and is sized to slidingly engage or be guided along the channel of the support. The cartridge includes a container having cavity for retaining a predetermined dose of the medicinal powder. Movement of the cartridge along the channel permits the cavity of the cartridge to align with the aperture of the support for the channel. Moreover, a cover may be placed on the cartridge to cover the cavity containing the powder drug to maintain sterility and to prevent contamination of the medicament. The support may further comprise means for removing the cover to permit the cavity to communicate directly with the aperture of the support channel. Such means may take the form of an edge on the channel which engages the cover and peels off the same continuously as the cartridge is advanced along the channel until alignment of the cavity and the aperture of the channel occur. At this juncture, the mere injection of gaseous propellant into the system of the present invention will educe or draw powder medicament from the cavity of the cartridge, mix the powder medicament with the propellant and air for delivery of a measured dose to the user in the form of a low velocity, soft, evenly dispersed aerosol.

It may be apparent that a novel and useful medicinal powder delivery system has been hereinabove described.

It is therefore an object of the present invention to provide a medicinal powder delivery system which delivers powder drugs in a homogeneous aerosol that is easy to administer to a patient.

Another object of the present invention is to provide a medicinal powder delivery system which eliminates reagglomeration of powder medications in alveolar tissue.

Yet another object of the present invention is to provide a medicinal powder delivery system which is capable of delivering drugs in powder form absent contamination.

A further object of the present invention is to provide a medicinal powder delivery system which accurately meters the powder drug to produce an accurate and reproducible dose level of the same to the user.

A further object of the present invention is to provide a medicinal powder delivery system in which a conventional gaseous propellant is employed to maintain dispersion of the powder medication prior to use by a patient.

Another object of the present invention is to provide a medicinal powder delivery system which is easily controlled by the injection of gaseous propellant into the system.

Another object of the present invention is to provide a medicinal powder delivery system in which powder drugs are motivated at a controlled flow rate and are electrostatically charged to maintain the dispersion of such particles in an aerosol created thereby.

Another object of the present invention is to provide a medicinal powder delivery system in which premixing of the powder drug and the propellant is eliminated.

Another object of the present invention is to provide a medicinal powder delivery system in which the powder drug is loaded into a cartridge and sealed against contamination until activation of the system of the present invention.

Figure 1:
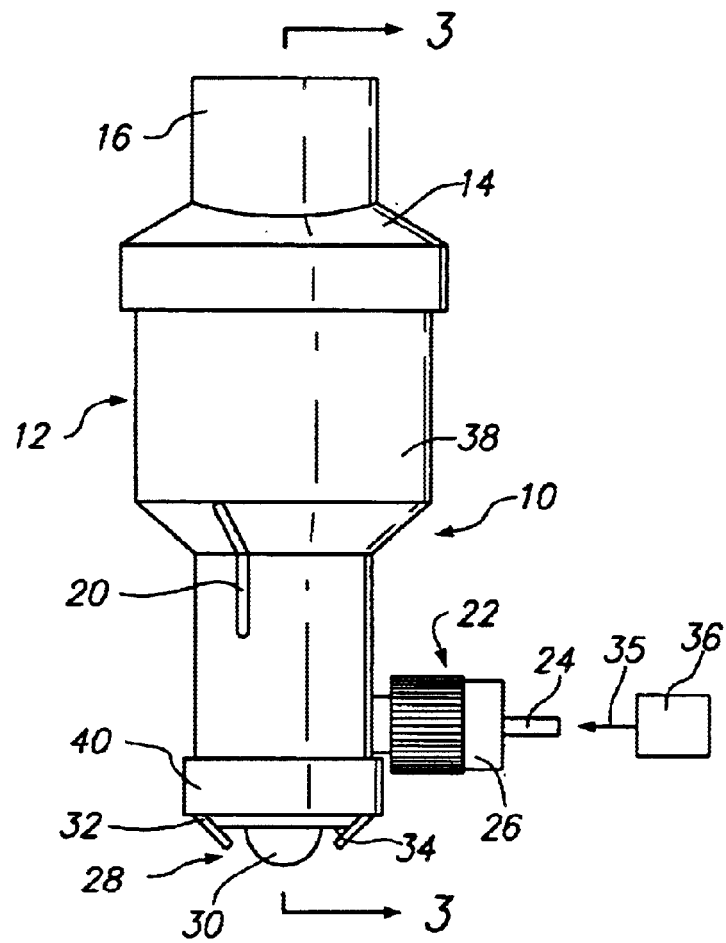
Figure 2:
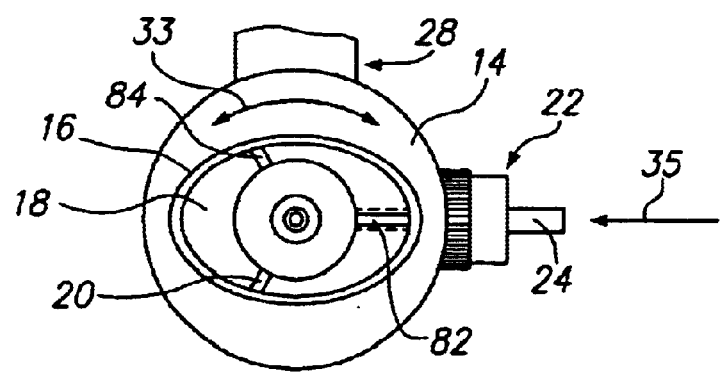
Figure 3:
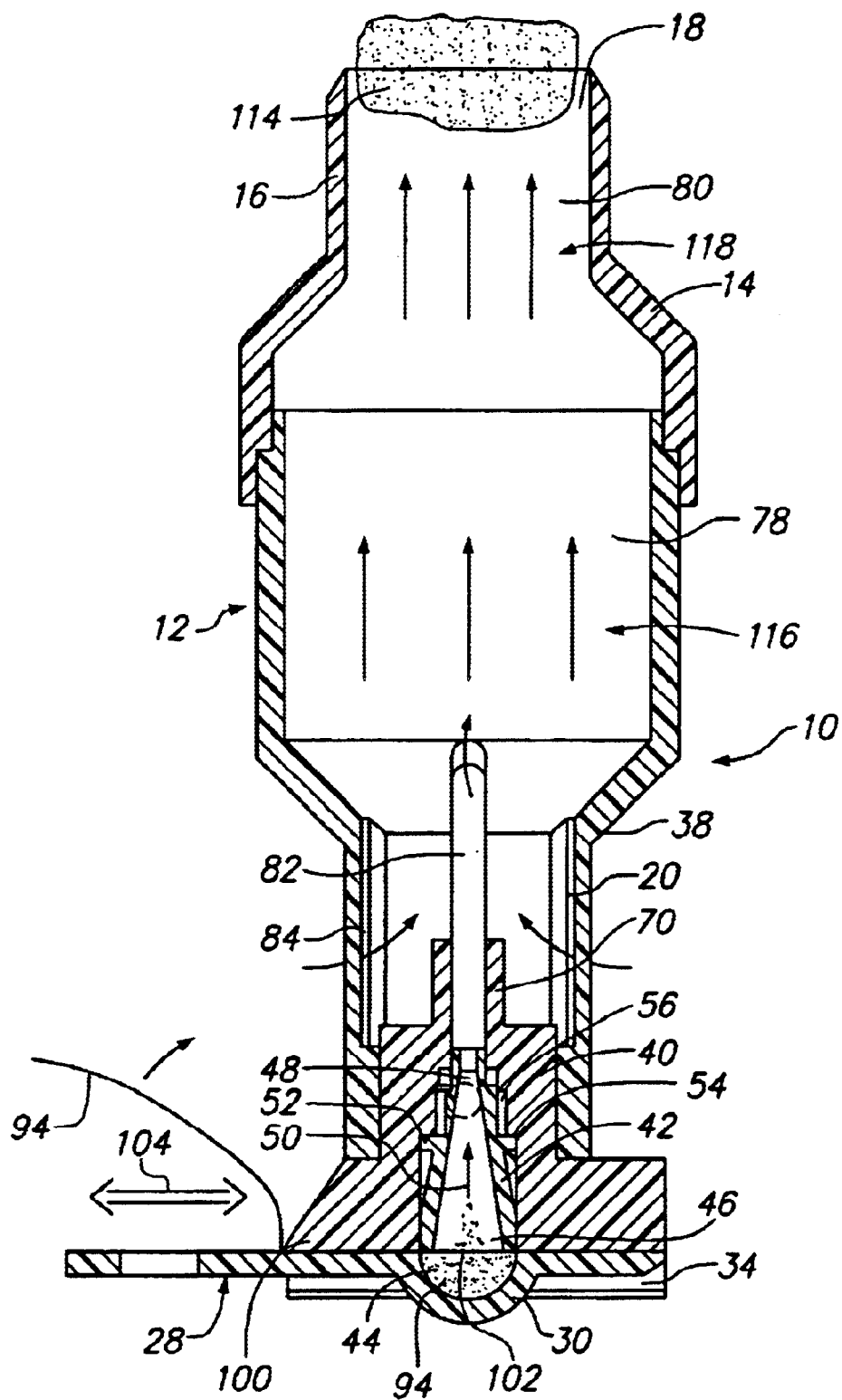
Figure 4:
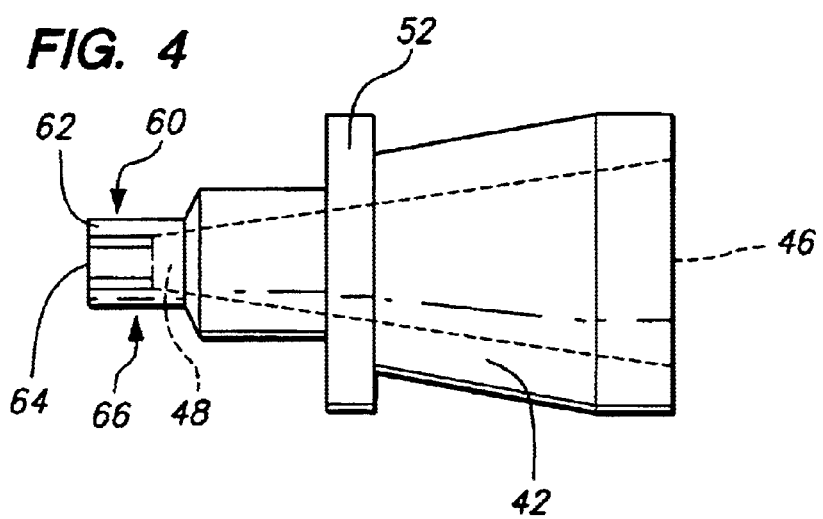
Figure 5:
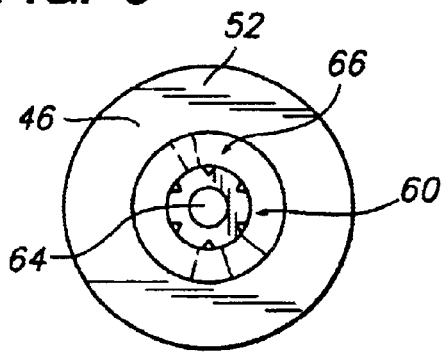
Figure 6:
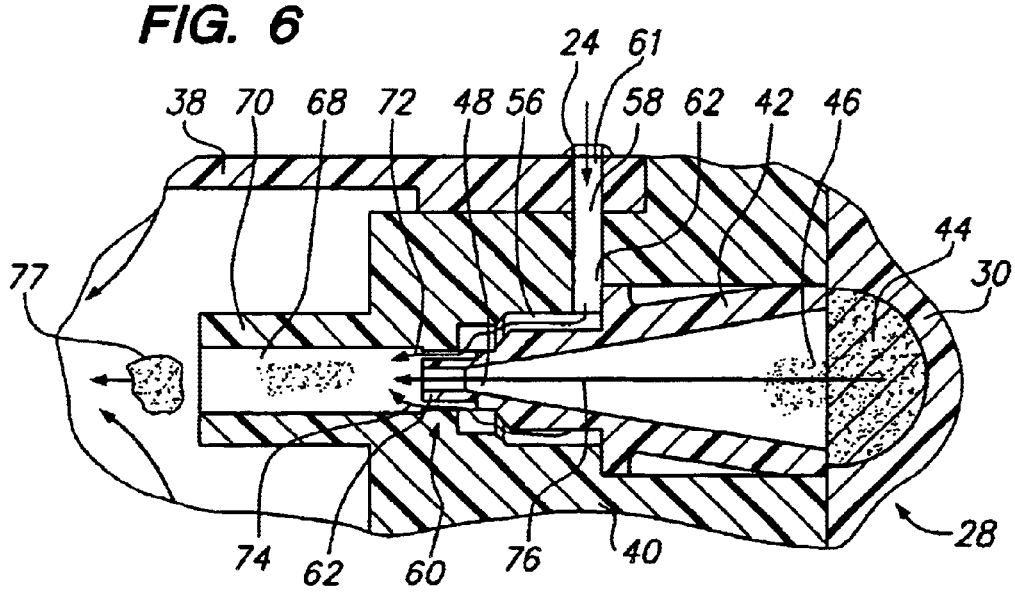
Figure 7:
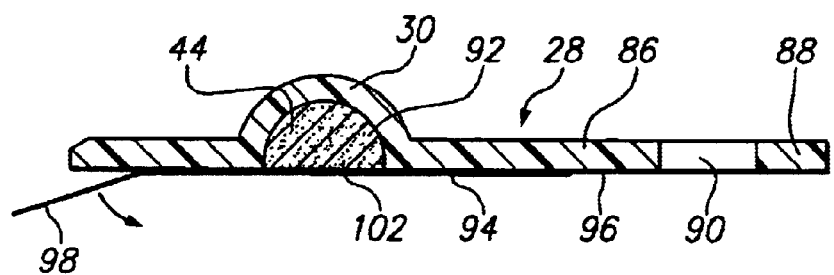
Figure 8:
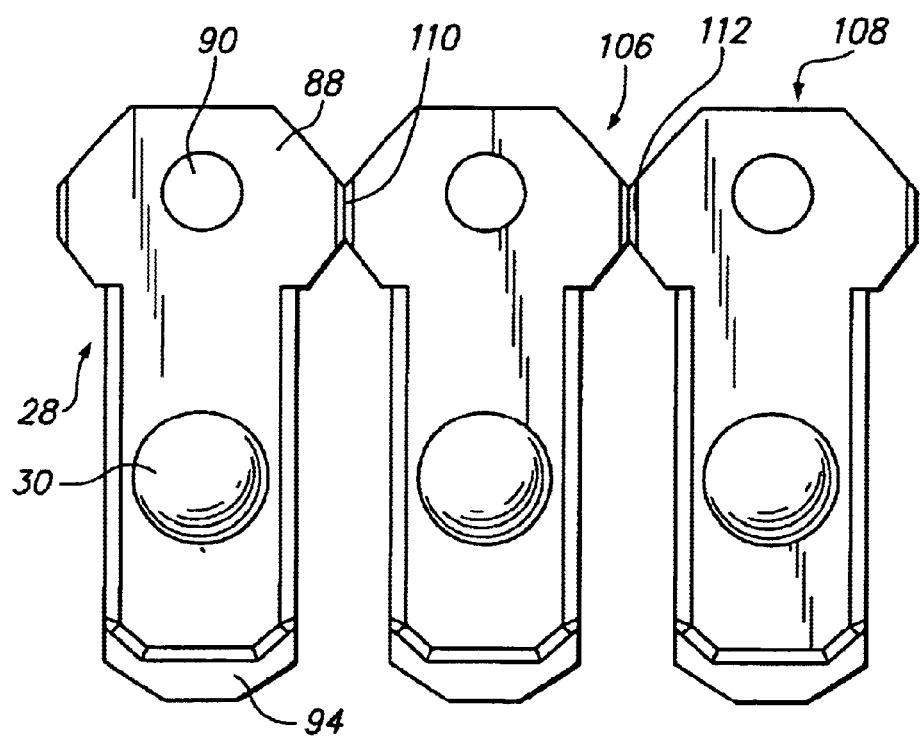

Another object of the present invention is to provide a medicinal powder delivery system in which the powder drug ingestion is easily synchronized with the breathing of the patient.

Another object of the present invention is to provide a medicinal powder delivery system which does not require the employment of electric motors or pumps to operate.

Another object of the present invention is to provide a medicinal powder delivery system which is formed into a compact configuration.

Another object of the present invention is to provide a medicinal powder delivery system which is capable of self-cleaning.

Another object of the present invention is to provide a medicinal powder delivery system which operates in an efficient manner and does not waste powdered medicine.

Another object of the present invention is to provide a medicinal powder delivery system which employs a stable vortex eddy field to create a homogeneous aerosol using a powder drug as the solid component.

Another object of the present invention is to provide a medicinal powder delivery system which does not require special training of the user patient to employ the same.

Another object of the invention is to provide a medicinal powder delivery system which facilitates dose counting.

The invention possesses other objects and advantages especially as concerns particular characteristics and features thereof which will become apparent as the specification continues.

BRIEF DESCRIPTION OF THE SEVERAL VIEWS OF THE DRAWING

FIG. 1 is a front elevational view of the device of the present invention.

FIG. 2 is a top plan view of the device of the present invention with the mouthpiece rotated 90 degrees.

FIG. 3 is a sectional view taken along line 3—3 of FIG. 1.

FIG. 4 is a side elevational view of the nozzle containing portion of the device of the present invention.

FIG. 5 is an enlarged left side view of the nozzle containing portion depicted in FIG. 4.

FIG. 6 is a sectional view of an enlargement of the powder and propellant mixing portion of the device of the present invention depicted in FIG. 3 and rotated 90 degrees.

FIG. 7 is a sectional view of a single cartridge containing powder medicament employed in the device of the present invention.

FIG. 8 is a top plan view of a trio of cartridges employed with the device of the present invention.

For a better understanding of the invention reference is made to the following detailed description of the preferred embodiments thereof which should be referenced to the prior described drawings.

DETAILED DESCRIPTION OF THE PREFERRED EMBODIMENTS OF THE INVENTION

Various aspects of the present invention will evolve from the following detailed description of the preferred embodiments thereof which should be referenced to the prior delineated drawings.

The preferred embodiment of the present invention is shown in the drawings in its entirety by reference character 10. Medicinal powder delivery system 10 includes as one of its elements a housing 12, FIG. 1. Housing 12 possesses a mouth piece 14 having an end portion 16 with an oval opening 18. Oval opening 18 is intended to pass the homogenized aerosol produced by system 10 and to contact the mouth of the user for inhalation of such aerosol. In addition, oval opening 18 tends to moderate the velocity of the aerosol leaving system 10 to a certain degree. Slit 20 serves as an entrance to the interior of housing 12 and is intended to be one of a plurality of slits which allows air to enter housing 12, the purpose of which will be discussed hereinafter. In addition, fitting 22 includes a nipple 24 and a rotatable sealing cap 26 which is compatible with a standard gaseous propellant source, such is one compatible with powder medicaments, i.e. compressed air and the like. In addition, cartridge 28 includes a spheroidal container for powder medicament which is slidably held by dovetail configured tracks 32 and 34. It should be noted that mouthpiece 14 is capable of rotating according to directional arrow 33, FIG. 2. Needless to say, mouth piece 14 has be rotated 90 degrees between the renditions shown in FIGS. 1 and 2. Directional arrow 35, FIGS. 1 and 2 indicates the flow of gaseous propellant from propellant source 36, depicted schematically in FIG. 1.

Referring now to FIG. 3 it may be seen that housing 12 includes a vessel 38 and a base portion 40 connected thereto. Base portion 40 provides a support location for guiding tracks 32 and 34 which extend therefrom to hold cartridge 28 in place. Also found within base portion 40 is a nozzle 42 which is intended to transport and accelerate the powder medicament 44 found within container 30 of cartridge 28. In this regard, nozzle 42 includes an entrance 46 of relatively wide configuration and an exit 48 of relatively narrow configuration. Directional arrow 50 indicates the motion of powder medicament 44 through nozzle 42. Flange 52 of nozzle 42 rests on shoulder 54 of base member 40 to form a passageway 56 for the gaseous propellant, best shown in FIG. 6.

Nipple 24, FIG. 1, of fitting 22 takes the form of a hollow member which conducts gaseous propellant to conduit 58 which communicates with passageway 56 FIG. 6. Thus, conduit 58 includes an entrance 61 and an exit 62 for passing gaseous propellant from source 36 to passageway 56, which lies adjacent nozzle exit 48.

Means 60 is also found in the present invention for shaping the flow characteristics of the gaseous propellant emanating from source 36 and traveling through conduit 58 and passageway 56. Such means may take the form of a cylindrical body 62 having a bore 64 which communicates with the exit 48 of nozzle 42. In addition, means 60 includes an outer surface with a plurality of grooves 66 which are constructed, in the preferred embodiment depicted in FIGS. 5–6, in a triangular cross-sectional configuration. Gaseous propellant emanating from source 36 and traveling through conduit 58 and passageway 56 is formed into a vortex field which passes into chamber 68 formed by boss 70 of base portion 40, directional arrows 72 and 74. Such movement of gaseous propellant into chamber 68 and the creation of the vortex field creates a sufficient vacuum (as much as 5 psi) by ejection to draw powder medicament from container 30, through nozzle 42 and into mixing chamber 68, directional arrow 76. Homogeneously mixed and electrostatically charged cloud of powder medicament 77 passes into interior 78 of vessel 38, to the interior 80, of mouth piece 14 and outwardly through oval opening 18 thereof for use. The powder medicament 48 stored in container 30 includes particles of a size ranging between 1 and 3 microns. Slits 20, 82, and 84 in the walls of vessel 38 permit air to mix thoroughly with the ejected propellant and medicinal powder 44 prior to exiting oval opening 18 of mouthpiece 16.

Referring now to FIGS. 7 and 8 it may be observed that cartridge 28 is depicted in greater detail. Cartridge 28 includes a main body 86 having a flared portion 88 which is intended to be gripped by the user. Opening 90 aids in this endeavor. Container 30 includes a cavity 92 which is enclosed by a cover 94 adhesively held to surface 96 of cartridge 28. Flap 98 of cover 94 is peeled away by edge 100 of base portion 40 when cartridge 28 is slidingly guided along channel members 32 and 34. Cavity 92 of container 30 includes an aperture 102 which communicates with entrance 46 to nozzle 42 when cartridge 28 is in place as depicted in FIG. 3. Directional arrow 104 illustrates the sliding movement of cartridge 38 between channel members 32 and 36, FIG. 3. As may be observed from FIG. 8, multiple cartridges, identical to cartridge 28 and exemplified by cartridges 106 and 108, may be connected to one another by frangible portions 110 and 112. Thus, cartridges 28, 106, and 108 are separable from one another for use with housing 12.

In operation, the user grasps cartridge 28 and slidingly engages channel members 32 and 34 of housing 12. Cartridge 28 is then pushed into the position shown in FIG. 3 to allow aperture 102 of container cavity 94 to communicate with entrance 46 of nozzle 42. Cover 94, which maintain the integrity and antiseptic condition of an aliquot amount of powder medicament 94, is peeled away by engagement of cover 94 with edge 100 of base member 40. To deliver a soft cloud 114 of powder medicament of the user through oval opening 18, gaseous propellant is directed through nipple 24, conduit 58, passageway 56, and into contact with means 60. The flow of the gas propellant is then shaped into a vortex eddy field which creates a very strong vacuum to educe powder medicament 44 through nozzle 42 and into chamber 68 where thorough mixing and charging occurs. The aerosol is then mixed with air in the interior 78 of vessel 38, directional arrows 116, FIG. 3 and into mouth piece interior 80, directional arrows 118. At this point, the user breathes the homogeneous aerosol cloud 114 of an accurate does of powder medicament, air and propellant to treat medical conditions such as asthma and the like. Interior 78 is also rendered free of powder medicament through this procedure.

While in the foregoing, embodiments of the present invention have been set forth in considerable detail for the purposes of making a complete disclosure of the invention, it may be apparent to those of skill in the art that numerous changes may be made in such detail without departing from the spirit and principles of the invention.

What is claimed is:

1. A medicinal powder delivery system utilizing a gaseous propellant source, comprising:

a. a nozzle including an entrance and an exit for passing the medicinal powder therethrough;

b. a conduit, said conduit including an entrance and an exit for passing the gaseous propellant therethrough, said conduit exit lying adjacent said nozzle exit;

c. means for shaping the flow characteristics of the gaseous propellant emanating from the gaseous propellant source, said means for shaping the flow characteristics of said gaseous propellant comprising a tube having an inner bore and an outer surface, said bore of said tube communicating with said conduit, said outer surface of said tube including a plurality of recesses for interacting with gaseous propellant emanating from the gaseous propellant source;

d. a vessel, said vessel including an entrance, an exit, and a chamber, said vessel entrance positioned adjacent said nozzle exit and said conduit exit to receive the medicinal powder, said plurality of recesses at said outer surface of said tube passing gaseous propellant to said chamber for mixing with the medicinal powder, said exit of said vessel permitting egress of said gaseous propellant and said medicinal powder.

2. The system of claim 1 in which said tube bore further comprises a first portion communicating with said nozzle exit and a second portion communicating with chamber of said vessel to allow passage of the medicinal powder from said nozzle exit and through said tube bore.

3. The system of claim 1 in which said vessel includes at least one vent opening between said entrance and exit thereof.

4. The system of claim 1 in which said vessel exit forms an oval cross-sectional configuration.

5. The system of claim 1 which further comprises:

a. a support including a channel, said channel having an aperture communicating with said nozzle; and b. a cartridge, said cartridge slidingly guided along said channel of said support, said cartridge including a cavity for retaining a predetermined dose of the medicinal powder, said cavity being alignable with said aperture of said support channel.

6. The system of claim 5 in which said tube bore further comprises a first portion communicating with said nozzle exit and a second portion communicating with chamber of said vessel to allow passage of the medicinal powder from said nozzle exit and through said tube bore.

7. The system of claim 5 in which said vessel includes at least one vent opening between said entrance and exit thereof.

8. The system of claim 5 in which said vessel exit forms an oval cross-sectional configuration.

9. The system of claim 5 in which said cavity includes a cover and said support further comprises means for removing said cover to permit said cavity to communicate with said aperture of said support channel.

10. The system of claim 9 in which said tube bore further comprises a first portion communicating with said nozzle exit and a second portion communicating with chamber of said vessel to allow passage of the medicinal powder from said nozzle exit and through said tube bore.

11. The system of claim 9 in which said vessel includes at least one vent opening between said entrance and exit thereof.

12. The system of claim 9 in which said vessel exit forms an oval cross-sectional configuration.

* * * * *